United States Patent [19]

Horrobin et al.

[11] Patent Number: 4,997,657

[45] Date of Patent: Mar. 5, 1991

[54] METHOD FOR IMPROVING SKIN SMOOTHNESS

[75] Inventors: David F. Horrobin; John C. M. Stewart, both of Guildford, England

[73] Assignee: Efamol Holdings, plc, Guildford, England

[21] Appl. No.: 321,204

[22] Filed: Mar. 9, 1989

[30] Foreign Application Priority Data

Mar. 22, 1988 [GB] United Kingdom ................. 8806737

[51] Int. Cl.[5] ............................................. A61F 13/00

[52] U.S. Cl. ..................................... 424/449; 424/456

[58] Field of Search ................................ 424/456, 449

[56] References Cited

U.S. PATENT DOCUMENTS 4,302,447 11/1981 Horrobin et al. .................. 514/560

4,568,343 2/1986 Leeper et al. ....................... 424/449

*Primary Examiner*—Merrell C. Cashion, Jr.

*Assistant Examiner*—Leon R. Horne

*Attorney, Agent, or Firm*—Nixon & Vanderhye

[57] ABSTRACT

A composition, particularly an oral composition, for improving the smoothness of the skin, wherein GLA or DGLA or both as such or in the form of physiologically acceptable and equivalent derivatives are brought into administrable form with a carrier or diluent.

6 Claims, 1 Drawing Sheet

GEOMETRIC EXPLANATION OF MEAN DEPTH OF ROUGHNESS (Rz). THE SCAN LENGTH L IS DIVIDED INTO FIVE EQUAL SEGMENTS, AND $R_Z$ IS THE MEAN OF THE MAXIMUM PEAK-TO-VALLEY HEIGHT FOUND IN EACH OF THE FIVE SEGMENTS.

$Z_1$ $Z_2$ $Z_3$ $Z_4$ $Z_5$

L/5 L/5 L/5 L/5 L/5

L

GEOMETRIC EXPLANATION OF MEAN DEPTH OF ROUGHNESS (Rz). THE SCAN LENGTH L IS DIVIDED INTO FIVE EQUAL SEGMENTS, AND $R_Z$ IS THE MEAN OF THE MAXIMUM PEAK-TO-VALLEY HEIGHT FOUND IN EACH OF THE FIVE SEGMENTS.

METHOD FOR IMPROVING SKIN SMOOTHNESS

FIELD OF THE INVENTION

The invention relates broadly to compositions of gamma-linolenic acid (GLA) and dihomo-gamma-linolenic acid (DGLA) for use in improvement of the skin.

BACKGROUND

Much interest has been shown in essential fatty acids (EFAs) and particularly GLA in recent years, both in relation to prostaglandin (PG) metabolism and generally for the functions of the acids in cell membranes and elsewhere in the body themselves. The two common series of EFAs are the n-6 series, metabolites of linoleic acid, and the n-3 series, metabolites of alphalinolenic acid. The structures and naming of the acids may for example be found in the applicant's published European Patent Specification No. 0132089 (84304610.3). The same specification also contains a discussion of the role of GLA as precursor of 1-series PGs and arachidonic acid as a precursor of 2-series PGs. This discussion is brief but is given at length in earlier applications also referred to and reference may be made to these for the whole background.

CURRENT DISCOVERY

The smoothness of human skin is widely regarded as a desirable characteristic in both sexes, but particularly in females. Many skin care preparations and cosmetics claim to make skin more smooth or less rough but few if any of these claims are backed by proper scientific experimental evidence.

Essential fatty acids (EFAs) of the linoleic acid series are well known to be required for normal skin structure and function. These EFAs are also known as n-6 or omega-6 fatty acids. When they are eliminated from the diet, the skin becomes structurally and functionally abnormal in many ways. The parent EFA, linoleic acid, in order to fulfill its full biological functions in the skin must be metabolised within the body for example to GLA, dihomo-gamma-linolenic acid (DGLA) and arachidonic acid (AA). The conversion of linoleic acid to GLA, and DGLA to AA, cannot take place in the skin, whereas the conversion of GLA to DGLA can occur in the skin. The formation of GLA from linoleic acid, and of AA from DGLA must take place in other body tissues, notably the liver, from which the required fatty acids are transported to the skin.

The conversion of linoleic acid to GLA is a ratelimiting step which is slow at the best of times. It can be further inhibited by a variety of factors including diabetes, aging, zinc deficiency, excess alcohol consumption, high levels of cholesterol, certain viral infections and catecholamines released during stress. People who have inherited an atopic disposition (atopics) which makes them liable to develop eczema, asthma, allergic rhinitis or other allergies are less able to convert linoleic acid to GLA than other people.

The inventors have unexpectedly found that there are a number of reasons why it is appropriate for the purpose of improving the smoothness of the skin to administer GLA, or the immediate product of it DGLA, directly rather than rely on the formation of GLA within the body. As far as the inventors are aware, no evidence which is scientifically valid and which demonstrates that administration of GLA is able to make apparently normal skin more smooth, has ever been presented.

In metal working a number of techniques have been developed to enable the smoothness of a surface to be measured completely objectively. Two of these techniques have now been applied to the measurement of the smoothness of human skin.

In one technique a light of standard intensity is shone on the surface at a standard angle. This light creates shadows whose intensity varies with the depth of the depressions in the skin surface. Under standard conditions a photograph is then taken of a specified area of the surface. This photograph is then objectively scanned by a densitometer to determine the depth of the shadows. The output of the densitometer is then converted into a profile which accurately represents the skin's surface.

In an alternative technique, known as the "stylus technique", an accurate impression of the contours of a surface is taken by means of silicon rubber or other appropriate material. This impression is then peeled off the surface and provides a mirror image. The impression is mounted under standard conditions and a stylus is set up to traverse a particular specified length of the impression. As the stylus traverses the impression, its vertical movements are translated into an electrical signal which in turn is transformed into an accurate representation of the contours of the surface.

Both these techniques have been used by the inventors to demonstrate that GLA is able to improve the smoothness of the surface of human skin.

Figure 1:
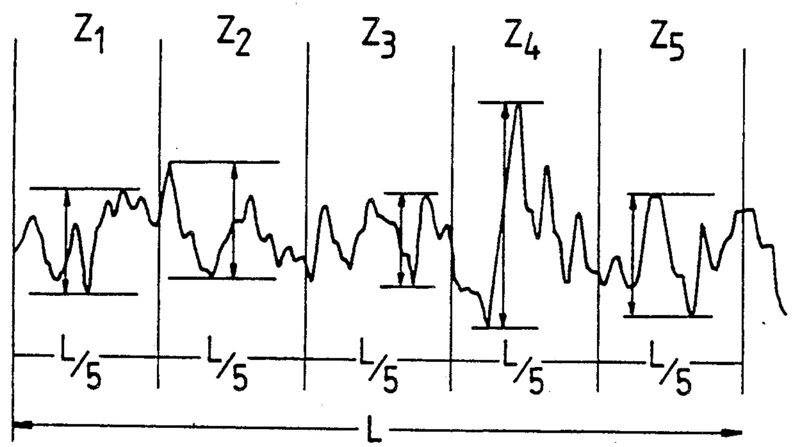
FIG. 1 illustrates the mean surface roughness of the skin measured.

In one study in which skin smoothness was measured by the stylus technique, 24 normal individuals and 35 individuals with atopic eczema took part. The technique was used to measure the smoothness of a specified area of skin on the ventral forearm. In the patients with atopic eczema, this area was chosen because it was not affected by the dermatitis and because superficially it appeared to be normal skin. The skin roughness parameter Rz was measured. The meaning of this is shown in the accompanying Figure. In essence, a standard length L of skin is specified and is divided into five equal parts. Within each part, the maximum peak to trough height is measured: Rz, the mean surface roughness, is the mean value for the five peak to trough values.

The results of this study are shown in the Table. As can be observed, prior to any treatment, the apparently normal skin in the individuals with atopic eczema was significantly rougher than the apparently normal skin in the normal people ($p<0.01$). Both the normal individuals and those with atopic eczema were then given 240 mg of GLA per day in the form of capsules of evening primrose oil for a period of four weeks. At the end of this period the roughness of the same specified area of skin was again measured. The roughness was reduced (or the smoothness increased) in both the normal individuals ($p<0.01$) and in the individuals with atopic eczema ($p<0.0001$). At the end of this period there was no difference between the smoothness of the skin in the normal individuals and in the individuals with atopic eczema.

TABLE 1

Roughness parameter, Rz, in arbitrary units in normal individuals and in individuals with atopic eczema, before and after the administration for four weeks of 240 mg of GLA per day.

| | NORMAL | ATOPIC | SIGNIFICANCE OF DIFFERENCE |
|---|---|---|---|
| Baseline | 64.7 + 1.1 | 72.4 + 1.4 | $p < 0.01$ |
| After GLA | 61.5 + 0.5 | 61.6 + 1.1 | not significant |
| Significance of change | $p < 0.01$ | $p < 0.0001$ | |

In another study, 31 individuals with atopic eczema were investigated. The smoothness of the ventral surface of the forearm was assessed by photography and densitometry. 16 of the individuals were treated for 12 weeks with 320 mg per day of GLA in the form of evening primrose oil capsules, while 15 individuals were treated with identical-appearing placebo capsules. The skin smoothness was measured at the beginning and the end of the study. In the GLA treated group, the mean fall in an arbitrary roughness parameter was 1.4 arbitrary units, starting from a mean baseline value of 10.5 ($p<0.01$). In contrast, in the placebo group there was a mean increase in roughness of 0.5 units, starting from a mean baseline value of 10.7. The difference between the improvement in the GLA group and the deterioration in the placebo group was significant at $p<0.01$.

THE INVENTION

The invention therefore depends on the use of GLA for improving the smoothness of the skin. Since GLA is rapidly converted to DGLA in the body, and since DGLA has effects similar to those of GLA, DGLA can optionally partially or fully replace the GLA in compositions according to the present invention. General reference to GLA herein is therefore to be understood accordingly as including DGLA, and also mixtures of GLA and DGLA.

More specifically, the invention, applicable to both healthy individuals and those where a disease condition affecting skin smoothness is present, lies in:

(1) The use of GLA or DGLA or both, as such or in the form of physiologically acceptable and equivalent derivatives for the manufacture of a medicament for improving the smoothness of the skin.

(2) Methods of improving the smoothness of the skin, wherein GLA or DGLA or both, as such or in the form of physiologically acceptable and equivalent derivatives are administered.

(3) A composition for improving the smoothness of the skin, wherein GLA or DGLA or both, as such or in the form of physiologically acceptable and equivalent derivatives are brought into administrable form with a carrier or diluent.

Systemic, particularly oral administration is preferred and dose ranges for it may be 1 mg to 100 g per day, preferably 20 mg to 2 g per day, more preferably 50 mg to 500 mg per day, calculated as GLA or DGLA.

Dose ranges for topical administration may be concentrations of 0.001 to 20% by weight in a topical base, diluent or carrier, preferably 0.01 to 10% by weight and more preferably 0.05 to 3% by weight, calculated as GLA or DGLA.

FORMS AND SOURCES

The GLA can be and indeed normally will be used as an assimilable, pharmaceutically acceptable and physiologically equivalent derivative and general reference to GLA is to be taken as including reference to such derivatives. DGLA may also be used in derivative form. Identification of useful derivatives is by their having the valuable effect in the body of the acid itself, but conversion can be shown directly by gas chromatographic analysis of concentrations in blood, body fat, or other tissue by standard techniques, for example those of Pelick et al, p. 23, "Analysis of Lipids and Lipoproteins" Ed. Perkins, American Oil Chemists Society, Champaign, Ill., U.S.A.

Convenient derivatives of GLA and DGLA include salts, amides, alcohols, esters including glyceride esters and alkyl (e.g. $C_1$ to $C_4$) esters, and phospholipids. The alcohols (—COOH of the parent acid represented by —$CH_2OH$) are equivalent in the sense of having valuable effect.

Thus if desired, pharmaceutical compositions may be produced for use in the invention by associating the natural or synthetic acid, as such or as a derivative, with an acceptable pharmaceutical vehicle. It is, however, at present convenient to incorporate the acids into compositions in the form of available oils having a high content of the acids, hence references to "oils" herein.

At the present time known natural sources of oils having a high GLA acid content are few (there are no known natural sources of significant amounts of DGLA). One source of oils currently available is the seed of Evening Primrose species such as *Oenothera biennis L.* and *Oenothera lamarckiana,* the oil extract therefrom containing GLA (about 8%) and linoleic acid (about 72%) in the form of their glycerides together with other glycerides (percentages based on total fatty acids). Other sources of GLA are Borage species such as *Borago officinalis* which, though current yield per acre is low, provide a richer source of gamma-linolenic acid than Oenothera oil, and seed oils from blackcurrant or other members of the Ribes family. Recent studies on storage oils of algae and fungi such as Spirulina spp, Rhizopus spp or Mortierella spp, which can be cultivated by fermentation promise other oil sources. Synthesis of GLA and DGLA is difficult but not impossible and provides another source.

The oil is extracted from the seeds, algae or fungi by one of the conventional methods of extraction such as cold pressure, screw pressure after partially cooking or solvent extraction.

Fractionation of a typical sample of evening primrose oil in the form of methyl esters shows the relative proportions:

| | |
|---|---|
| Palmitate | 6.15 |
| Stearate | 1.6 |
| Oleate | 10.15 |
| Linoleate | 72.6 |
| Gamma-Linolenate | 8.9 |

As preservative, alpha-tocopherol is added to the oil in a concentration 0.1%.

The seed oil extracts referred to above can be used as such or can, for example, if desired, be fractionated to yield an oily composition containing the triglycerides of gamma-linolenic and linoleic as the main fatty acid components, the gamma-linolenic acid content being if desired a major proportion. Seed oil extracts appear to have a stabilising effect upon dihomo-gamma-linolenic acid if present.

DIETARY COMPOSITIONS

The invention is chiefly described in relation to methods of treatment and pharmaceutical compositions, but it will be understood that the GLA, being in the nature of a dietary supplement, could be incorporated in a dietary margarine or other foodstuff.

PHARMACEUTICAL PRESENTATION

The compositions according to the invention are conveniently in a form suitable for systemic including oral, parenteral, or any other form of administration in which the fatty acids reach the skin through the bloodstream, or topical administration, in a suitable pharmaceutical vehicle, as discussed in detail for example in Williams British Patent Specification No. 1,082,624 to which reference may be made, and in any case very well known generally for any particular kind of preparation. The compositions, for example, may be for oral administration in which case they may be in the form of tablets, capsules, enteric-coated tablets or capsules to avoid damage by the acid environment of the stomach, syrups, drinks or any other appropriate dose format. Alternatively, the compositions may be for parenteral administration in which case they may be in the form of intra-muscular, sub-cutaneous, intravenous, intraperitoneal or other appropriate route. Injectable solutions of hydrolysed Oenothera oil may be prepared using albumin to solubilise the free acid. GLA or DGLA are absorbed through the skin surface and so topical administration may be via creams, lotions, ointments, packs, masks, sticks or any other appropriate skin care or cosmetic formulation.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

The following are specific examples of the invention, for use in improving smoothness of the skin in man:

EXAMPLE 1

The following are specific examples of the invention, for oral administration to persons requiring improvement to skin smoothness:

A. 250 mg gelatin capsules of evening primrose oil containing 20 mg GLA, 3/day.
B. 500 mg gelatin capsules of borage oil containing 120 mg GLA, 4/day.
C. 100 mg gelatin capsules of pure GLA, 4/day.
D. 50 mg gelatin capsules of pure DGLA, 6/day.
E. 300 mg gelatin capsules of ethyl-GLA, 8/day.
F. 500 mg gelatin capsules of blackcurrant seed oil containing 90 mg GLA, 10/day.

Alternatives are capsules of corresponding amounts of oil from fungal or algal sources containing between 8% and 20% GLA. Further alternatives are capsules containing synthetic salts, amides, alcohols or esters of GLA or DGLA administered in molar equivalent amounts.

EXAMPLE 2

The following is an example of a skin cream containing GLA as the natural glyderide of evening primrose oil, the manufacturing formula being:

| | % w/w |
|---|---|
| Evening primrose oil | 20.0 |
| Base cream ingredients, e.g. glyceryl monostearate, isopropyl myristate and beeswax | 14.0 |
| Humectant, e.g. propylene glycol | 4.0 |
| Stabiliser, e.g. magnesium aluminium silicate | 2.0 |
| Emulsifier | 5.0 |
| Preservative | 0.65 |
| Anti-oxidant | 0.1 |
| Deionised water/citric acid monohydrate/ disodium hydrogen phosphate | to 100 to adjust to approx. pH4. |

EXAMPLE 3

The following is an example of a moisture cream for the skin, the manufacturing formula being:

| | % w/w |
|---|---|
| Evening primrose oil | 5.0 |
| Humectant, e.g. glycerine | 5.6 |
| Emulsifier | 2.69 |
| Gelling agent | 1.50 |
| Preservative | 0.75 |
| Anti-oxidant | 0.71 |
| Emollient | 10.33 |
| Perfume (if required) | 0.4 |
| Deionised water | to 100 |

Use of the cream

Using the techniques described earlier, the effects of topical application of the above cream were investigated.

In ten patients with dry skin, impressions of the arm skin surface were taken and measured by profilometry. The cream was then applied to the skin twice per day for 28 days. Skin profiles were repeated on days 1, 3, 7, 14, 21 and 28, and again on day 31, three days after stopping treatment. Prior to taking a skin profile the skin was washed to ensure that there was no residual cream. Moreover, profiles were taken at least two hours after the last application of the cream.

The results were initial FIG. 86, day 1 to 28 FIGS. 82, 80, 79, 76.5, 75, 74, day 31 FIG. 74 (the figures are in arbitrary units). Topical application produced a progressive improvement in skin smoothness which was very rapid in the first week, but which had still not reached a final plateau after 28 days. There was no rapid reversal of the smoothness three days after stopping the cream showing that the change in skin smoothness could not-be attributed to any local mechanical effect of the cream.

From the above description, it will be appreciated that in the claims below the term "smoothness of the skin" is to be interpreted not in any subjective visual or tactile sense but in objective terms of peak and trough variation of the pitch of the skin surface about a mean position in a linear measurement transit.

I claim:

1. A method of improving the smoothness of healthy skin by topically applying to the affected skin a composition of GLA or DGLA or both or a physiologically acceptable and equivalent derivative, the acid(s) being present in a concentration of 0.01 to 20% by weight of the or each acid or molar equivalent amount(s) or derivative(s).

2. The method of claim 1, in which the acid(s) is present in a concentration of 0.01 to 10% by weight.

3. The method of claim 2, in which the acid(s) is present in a concentration of 0.05 to 3% by weight.

4. The method of claim 1, in which the composition is applied in an amount to give the daily amount of 1 mg to 100 g of the acid(s) or derivative(s).

5. The method of claim 4, in which the daily amount administered is from 20 mg to 2 g.

6. The method of claim 5, in which the daily amount administered is from 1 mg to 500 mg.

* * * * *

US004997657B1

REEXAMINATION CERTIFICATE (2553rd)

United States Patent [19]

[11] B1 4,997,657

Horrobin et al.

[45] Certificate Issued May 2, 1995

[54] METHOD FOR IMPROVING SKIN SMOOTHNESS

[75] Inventors: David F. Horrobin; John C. M. Stewart, both of Guilford, England

[73] Assignee: Efamol Holdings plc., Guildford, England

Reexamination Request:
No. 90/002,775, Jul. 9, 1992

Reexamination Certificate for:

| | |
|---|---|
| Patent No.: | **4,997,657** |
| Issued: | **Mar. 5, 1991** |
| Appl. No.: | **321,204** |
| Filed: | **Mar. 9, 1989** |

[30] Foreign Application Priority Data

Mar. 22, 1988 [GB] United Kingdom ................ 8806737

[51] Int. Cl.[6] ................................ A61K 7/48
[52] U.S. Cl. ................................ 424/401; 424/449; 424/456
[58] Field of Search ................ 424/401, 456, 449

[56] References Cited

PUBLICATIONS

Jiji Press, Ltd., Jun. 11, 1986.
Chemical Week, Dec. 24, 1986, p. 9.
Baltimore Business Journal, Jun. 15, 1987.
United Press International, Dec. 8, 1982.
The Financial Times Limited, Sep. 23, 1985.
Cosmetic and Toiletries, vol. 99, May, 1984.
Kirk Othner Encyclopedia of Chemical Technology, 1980, p. 800.
Save Your Money, Save Your Face, 1986, pp. 293, 341.
Cosmetics: What The Ads Don't Tell You 1977.
Japan Watch, vol. 6, No. 22, Nov. 17, 1986, p. 6.
Japan Watch, vol. 6, No. 20, Oct. 20, 1986, p. 6.
COMLINE Daily News Biotechnology and Medical Technology, Jun. 13, 1986.
Jiji Press, Ltd. Feb. 5, 1986.
Efamolia Evening Primrose Oil Advertisement, Apr., 1986.
Efamolia Evening Primrose Oil Advertisement, Apr., 1986.

*Primary Examiner*—Thurman K. Page

[57] ABSTRACT

A composition, particularly an oral composition, for improving the smoothness of the skin, wherein GLA or DGLA or both as such or in the form of physiologically acceptable and equivalent derivatives are brought into administerable form with a carrier or diluent.

REEXAMINATION CERTIFICATE ISSUED UNDER 35 U.S.C. 307

THE PATENT IS HEREBY AMEMDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-6 dependent on an amended claim, are determined to be patentable.

1. A method of improving the smoothness of healthy skin by topically applying *daily* to the [affected] *healthy* skin a composition of GLA or DGLA or both or a physiolocially acceptable and equivalent derivative, the acid(s) being present in a concentration of 0.01 to 20% by weight of the or each acid or molar equivalent amount(s) or derivative(s).

* * * * *